(12) United States Patent
Lauf et al.

(10) Patent No.: US 10,524,836 B2
(45) Date of Patent: Jan. 7, 2020

(54) DYNAMIC STRUT FOR FIXATION CONSTRUCTS

(71) Applicant: Life Spine, Inc., Huntley, IL (US)

(72) Inventors: Garrett D. Lauf, Hampshire, IL (US); Matthew S. Coyne, Algonquin, IL (US)

(73) Assignee: Life Spine, Inc., Huntley, IL (US)

( * ) Notice: Subject to any disclaimer, the term of this patent is extended or adjusted under 35 U.S.C. 154(b) by 0 days.

(21) Appl. No.: 16/015,124

(22) Filed: Jun. 21, 2018

(65) Prior Publication Data
US 2018/0368887 A1 Dec. 27, 2018

Related U.S. Application Data

(60) Provisional application No. 62/522,888, filed on Jun. 21, 2017.

(51) Int. Cl.
*A61B 17/62* (2006.01)
*A61B 17/60* (2006.01)

(52) U.S. Cl.
CPC ........ *A61B 17/62* (2013.01); *A61B 2017/606* (2013.01)

(58) Field of Classification Search
CPC ....... A61B 17/62; A61B 17/64; A61B 17/645; A61B 17/66
USPC .................................................. 403/56, 122
See application file for complete search history.

(56) References Cited

U.S. PATENT DOCUMENTS

| | | | | |
|---|---|---|---|---|
| 4,714,076 A | * | 12/1987 | Comte | A61B 17/6458 606/57 |
| 2010/0312243 A1 | * | 12/2010 | Ross | A61B 17/62 606/56 |
| 2010/0331840 A1 | * | 12/2010 | Ross | A61B 17/62 606/54 |
| 2014/0135764 A1 | * | 5/2014 | Ross | A61F 5/042 606/57 |
| 2018/0344354 A1 | * | 12/2018 | Mullaney | A61B 17/62 |

* cited by examiner

*Primary Examiner* — Julianna N Harvey
(74) *Attorney, Agent, or Firm* — Foley & Lardner LLP

(57) ABSTRACT

A dynamic strut for external fixation constructs has first and second sub-struts that are axially adjustable in length and rotational position relative to one another, with the first sub-strut supporting a first dual universal joint with a first attachment peg for connection to an external fixator, and the second sub-strut supporting a second dual universal joint with a second attachment peg for connection to an external fixator. The first and second dual universal joints each include first and second ball-and-socket joints, whereby the associated attachment peg is adjustable in orientation. Set screws fix orientation of the attachment peg relative to the first ball-and-socket joint and the housing. Angular orientation of the first dual universal joint is fixed while angular orientation of the second dual universal joint is adjustable. The second sub-strut supports an axially movable shaft that supports the second dual universal joint. An adjustor allows the first and second sub-struts to axially translate relative to each other to increase or decrease length.

18 Claims, 8 Drawing Sheets

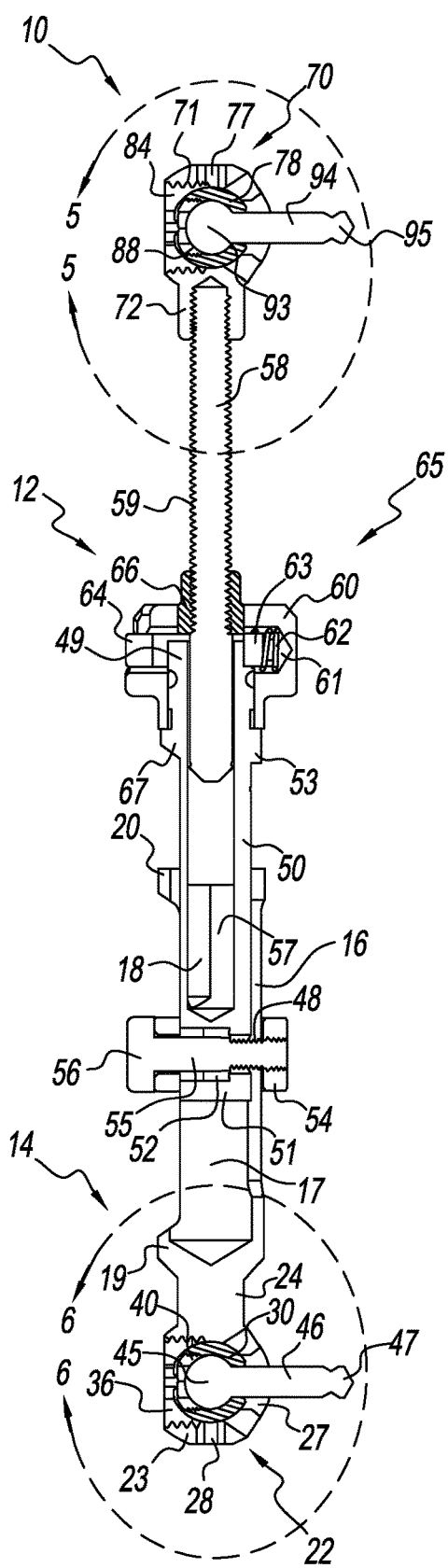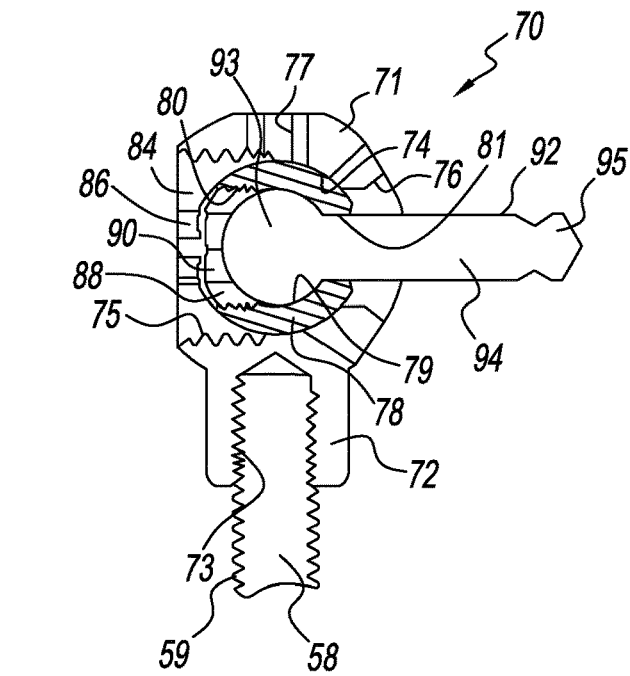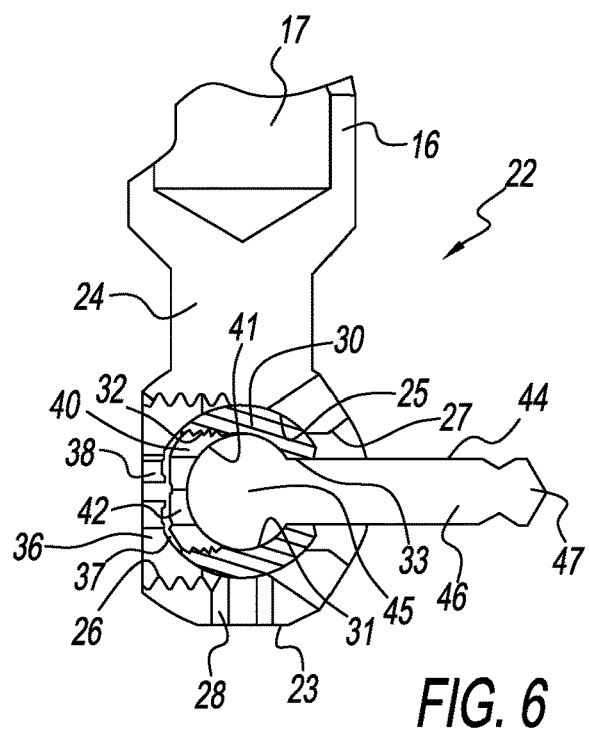
FIG. 4
FIG. 5
FIG. 6

DYNAMIC STRUT FOR FIXATION CONSTRUCTS

CROSS-REFERENCE TO RELATED APPLICATIONS

This U.S. non-provisional patent application claims the benefit of and/or priority under 35 U.S.C. § 119(e) to U.S. provisional patent application Ser. No. 62/522,888 filed Jun. 21, 2017 titled "External Fixator Strut," the entire contents of which is specifically incorporated herein by reference.

FIELD OF THE INVENTION

The present invention relates to components for external orthopedic fixation and, more particularly, to dynamic struts for external orthopedic fixation.

BACKGROUND OF THE INVENTION

External fixation, as an alternative to internal fixation, is a surgical approach to stabilize bone and soft tissues at a distance from the injury that uses fixation constructs known as external fixators. External fixation may be done for various bones and/or areas of the body such as, but not limited to, the arm, spine, leg, ankle, and foot. It provides unobstructed access to the relevant skeletal and soft tissue structures for their assessment and intervention(s) needed to restore bony continuity and a functional soft tissue cover.

In this kind of surgical approach, holes are drilled into uninjured areas of bones around the desired orthopedic problem/area and special bolts or wires are screwed into the holes. Outside the body, one or more rings surround the desired orthopedic area, the rings connected to one another by one or more struts having universal joints (e.g. a ball-and-socket joint) to make a rigid support. The orthopedic problem/area can be set in the proper anatomical configuration by adjusting the struts/universal (ball-and-socket) joints. A person skilled in the art will recognize that struts which provide the greatest amount of adjustability provide for a better external fixator. A better external fixator provides for better healing. It is thus important that the struts provide the greatest amount of adjustment in all planes, direction, and/or degrees.

Without being limiting, it is thus an object of the present invention to provide a dynamic strut for external fixator constructs that provides adjustment in all planes, directions, and/or degrees. It is further an object of the present invention to provide a strut for external fixators that allows for universal movement in all planes, directions, and/or degrees. These and other non-limiting objects are satisfied by the present invention.

SUMMARY OF THE INVENTION

A dynamic strut for external orthopedic fixation constructs has a first sub-strut or cylinder component and a second sub-strut or piston component for adjustable axial movement between the two components, and a dual universal ball-and-socket joint connector at the end of the piston component and a dual universal ball-and-socket joint connector at the end of the cylinder component for universal connection of the first sub-strut and the second sub-strut to fixation constructs (e.g. rings), at least one of the dual ball-and-socket joints being radially adjustable relative to its sub-strut.

The present dynamic strut provides for universal movement in all planes, directions, and/or degrees.

In particular, the present dynamic strut for external orthopedic fixators and fixation constructs has first and second components or struts that are axially adjustable in length and rotational position relative to one another, the first component supporting a first dual universal joint for connection thereof to an external fixation ring and having a first housing for a first ball-and-socket joint, the first housing fixed in radial orientation, the first ball-and-socket joint adjustable in orientation relative to the first housing and supporting a second ball-and-socket joint supporting a peg adjustable in orientation relative to the first ball-and-socket joint, a first set screw for fixing the orientation of the peg relative to the first ball-and-socket joint, and a second set screw for fixing the orientation of the first ball-and-socket joint relative to the first housing, the second component supporting a shaft axially movable relative thereto, the shaft supporting a second dual universal joint for connection thereof to an external fixation ring and having a second housing for a third ball-and-socket joint, the second housing adjustable in radial orientation, the third ball-and-socket joint supporting a fourth ball-and-socket joint supporting a second peg adjustable in orientation relative to the third ball-and-socket joint, a third set screw for fixing the orientation of the second relative to the third ball-and-socket joint, and a fourth set screw for fixing the orientation of the third ball-and-socket joint relative to the second housing. A C-clip or the like allows the first and second struts to translate relative to each other to increase or decrease length. Once this C-Clip is tightened the dynamic strut is then axially locked.

There is also a threaded plastic piece that is pinned into the top of the push button assembly. This interfaces with the threaded shaft.

Further aspects of the present invention will become apparent from consideration of the drawings and the following description of forms of the invention. A person skilled in the art will realize that other forms of the invention are possible and that the details of the invention can be modified in a number of respects without departing from the inventive concept. The following drawings and description are to be regarded as illustrative in nature and not restrictive.

BRIEF DESCRIPTION OF THE DRAWING FIGURES

The features of the invention will be better understood by reference to the accompanying drawings which illustrate a form of the present invention, wherein:

FIG. 4 is a side sectional view of the dynamic strut of FIG. 1;

FIG. 5 is an enlarged view of the upper end of the dynamic strut of FIG. 4 taken along circle 5-5 thereof;

FIG. 6 is an enlarged view of the lower end of the dynamic strut of FIG. 4 taken along circle 6-6 thereof;

DETAILED DESCRIPTION OF THE INVENTION

Figure 1:
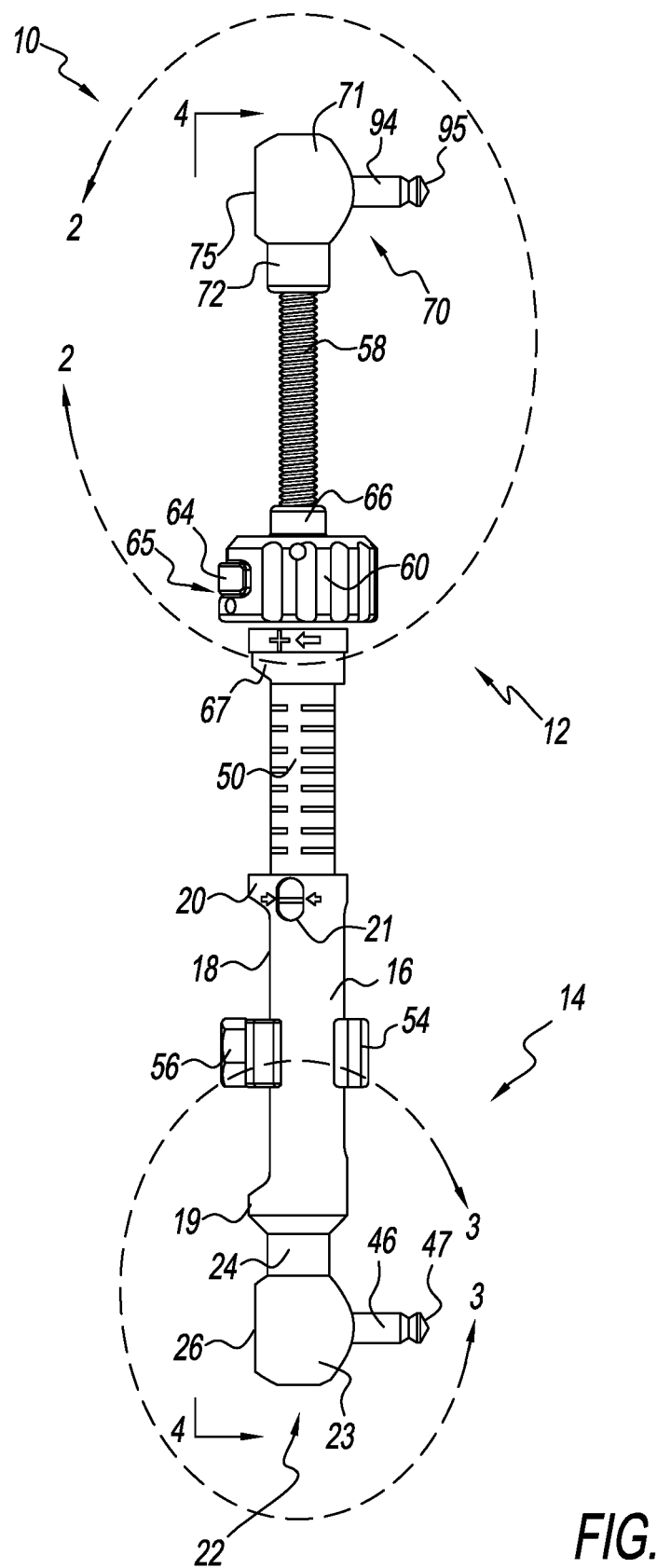
FIG. 1 is a side plan view of the present dynamic strut.
Figure 2:
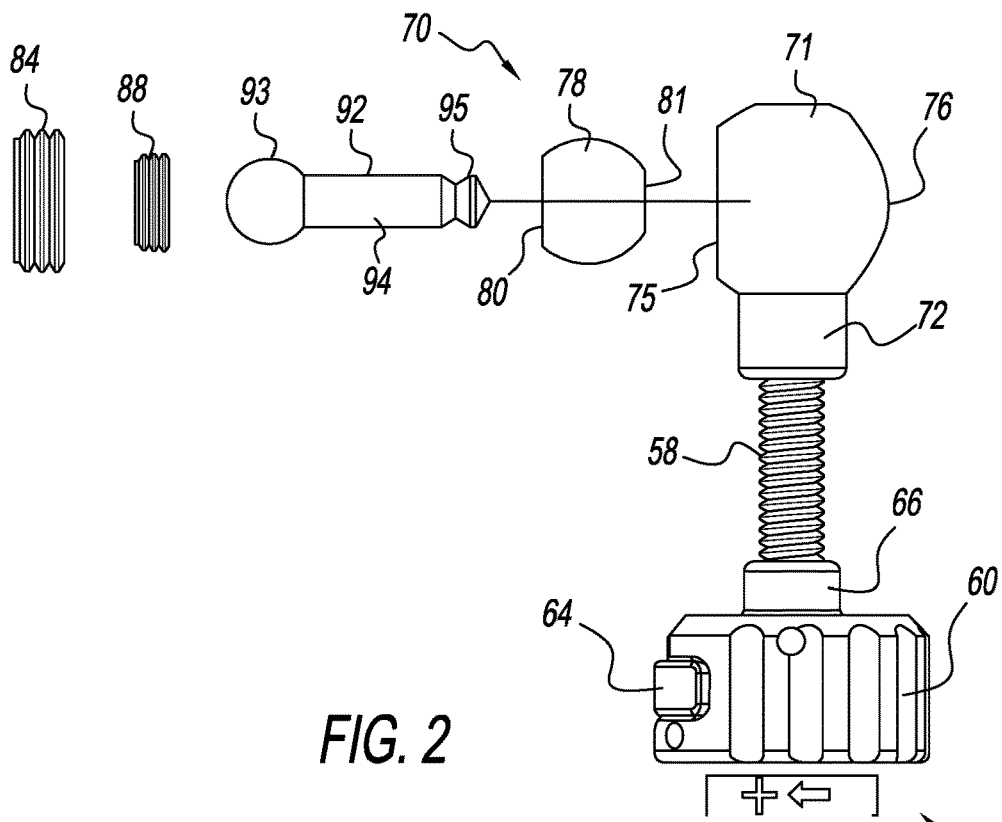
FIG. 2 is an enlarged view of an upper end of the dynamic strut of FIG. 1 taken along circle 2-2 thereof with its dual universal ball joint in an exploded view.
Figure 3:
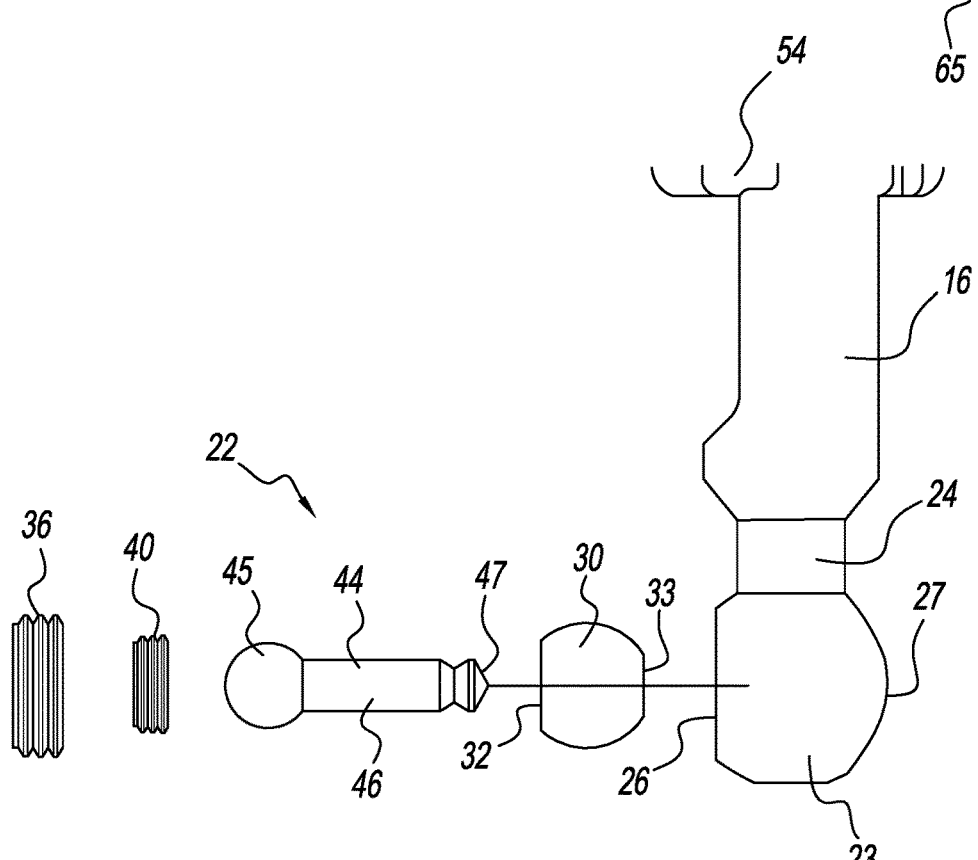
FIG. 3 is an enlarged view of a lower end of the dynamic strut of FIG. 1 taken along circle 3-3 thereof with its dual universal ball joint in an exploded view.
Figure 7:
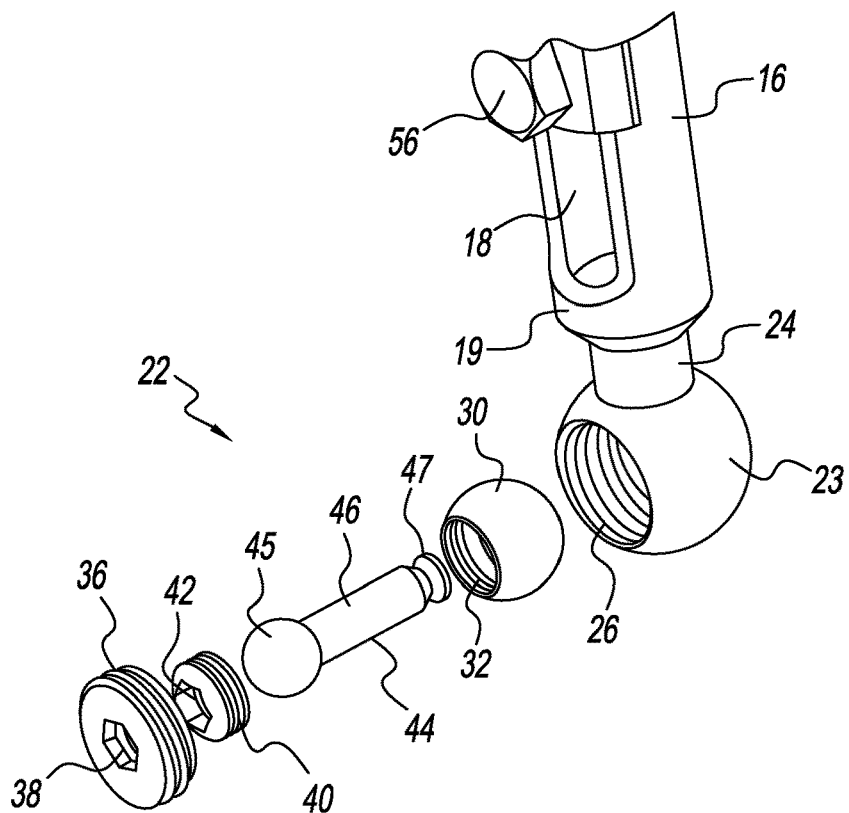
FIG. 7 is an enlarged exploded view of the dual universal ball joint of the lower end of the dynamic strut of FIG. 1.
Figure 8:
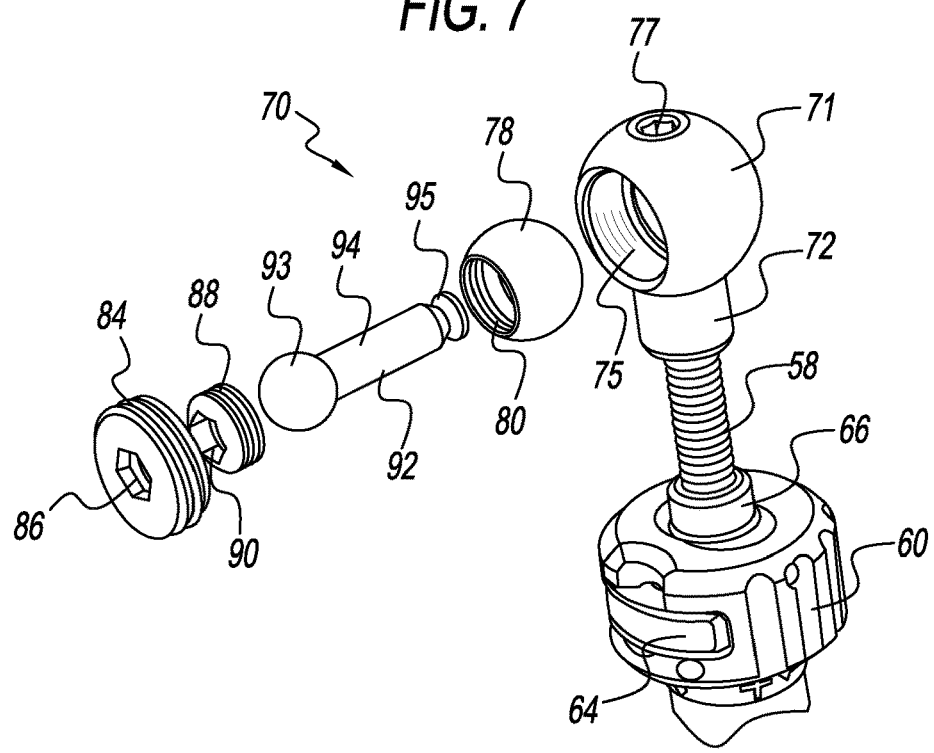
FIG. 8 is an enlarged exploded view of the dual universal ball joint of the upper end of the dynamic strut of FIG. 1.
Figure 9:
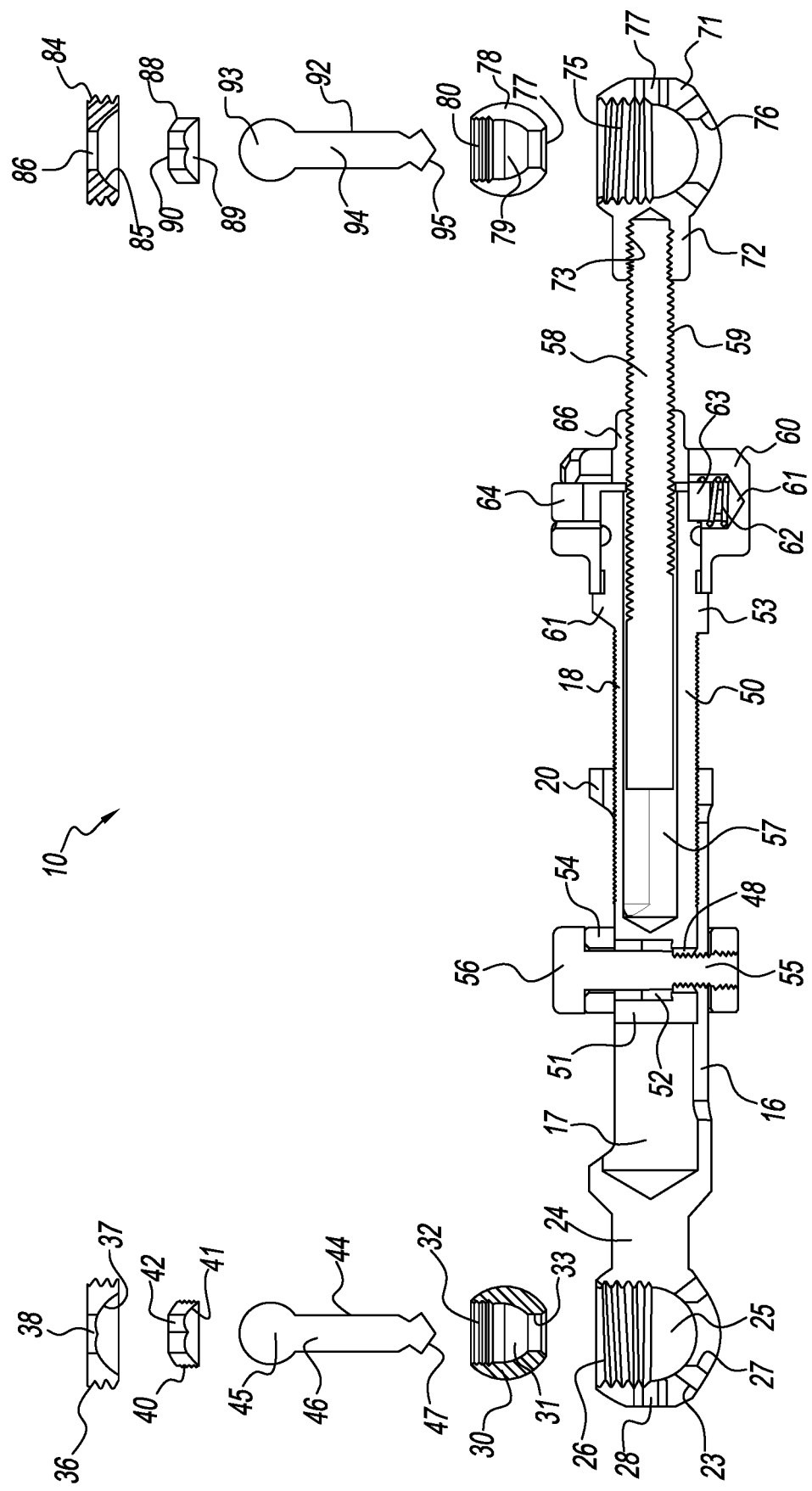
FIG. 9 is a side sectional view of the dynamic strut of FIG. 1 with the components of the upper and lower dual universal ball joints shown in an exploded view.
Figure 10:
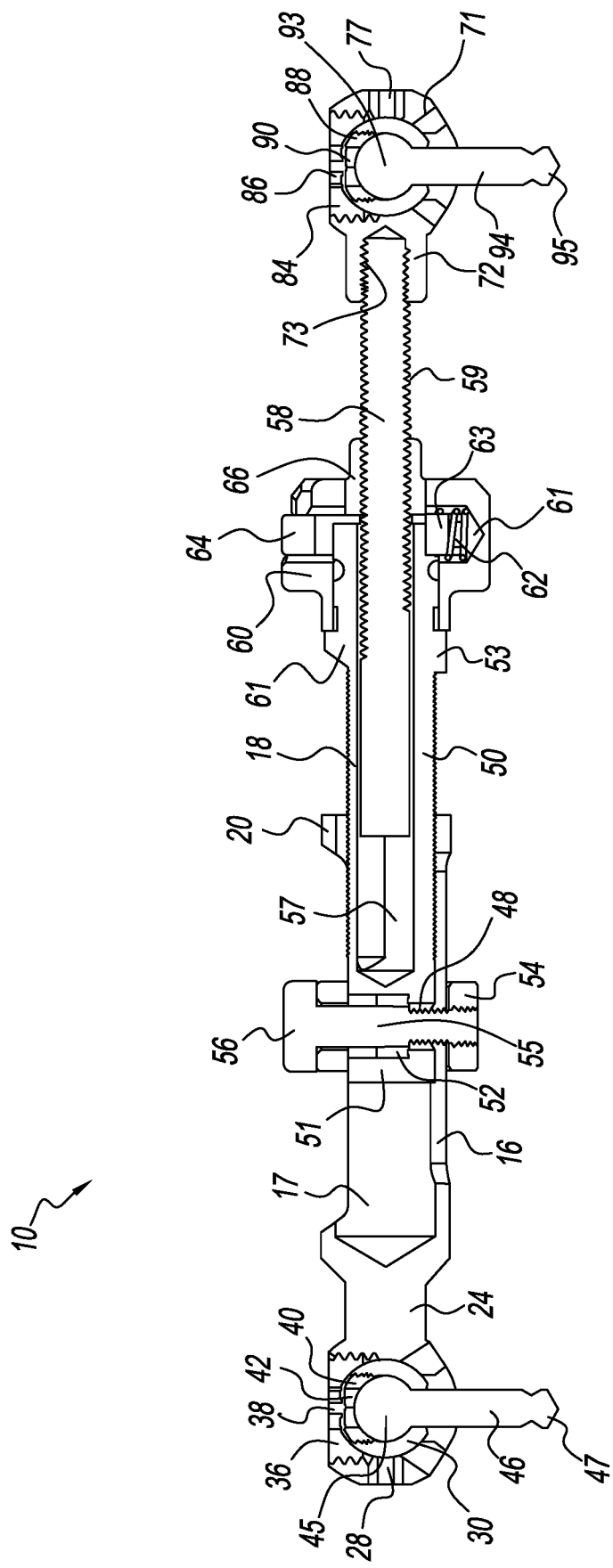
FIG. 10 is a side sectional view of the dynamic strut of FIG. 1.

Referring to FIGS. 1-10, there is shown various views of a dynamic strut/strut 10 for use in external orthopedic fixators/fixation constructs. The dynamic strut 10 shown in FIGS. 1-12 is designed to allow for a quick connection between two fixation rings (see FIGS. 11-12) or the like (i.e. components) of a fixation construct. The dynamic strut 10 is fashioned from a bio-compatible material such as is known in the art.

The strut 10 has a first or lower component or sub-strut 12 and a second or upper component or sub-strut 14, the nomenclature first and second being arbitrary. The second component 14 is characterized by a generally tubular body 16 defining a generally cylindrical interior or cavity 17 of a given axial length, an open top/top end, and a closed bottom/bottom end. A cutout 18 is provided along an axial side of the body 16 providing communication with the exterior and the interior 17 to define a lower lip, shelf, or ledge 19 and an upper lip, shelf, or ledge 20. The upper and lower lips 20, 19 provide upper and lower movement stops for the adjustor/band/clip 54. The length of the axial cutout 18 determines the amount of axial adjustment/travel of the first component 12 relative to the second component 14. A sight opening 21 is provided proximate the top of the body 16 for sighting demarcations/indications/indicators 50 on the first component 12 for determining adjusted axial length of the strut 10.

The bottom end of the tubular body 16 has a neck 24 supporting a dual universal/ball-and-socket joint 22, characterized by a spherical housing/head 23 extending from the neck 24 and having a spherical interior, cavity, or socket 25, a configured bore 28, a ball-and-socket joint 30 received for free rotation in the socket 25 and having a spherical interior, cavity, or socket 31, a peg or attachment member 44 having a spherical head 45 for free rotation receipt in the socket 31, a first set screw 36 for fixing rotational orientation of the ball-and-socket joint 30 relative to the head 23, and a second set screw 40 for fixing rotational orientation of the spherical head 45 of the peg 44. The attachment peg 44 is thus rotationally positionable relative to the ball-and-socket joint 30, while the ball-and-socket 30 is rotationally positionable relative to the head 23 for two-step or stage rotational orientation positioning of the attachment member 44 or the strut if the attachment member 44 is considered stationary.

The head 23 has a spherical interior/cavity/socket 25 and a threaded rear opening 26 and a non-threaded front opening 27. The rear opening 26 is threaded to receive the threaded set screw 36 (the set screw 36 having a configured socket 38 in its top surface), while the front opening 27 is not threaded to allow the shaft 46 and tip 47 of the peg 44 to extend therethrough and thus be universally rotationally and angularly positioned relative thereto. The set screw 36 has a spherical inner surface/seat 37. The ball-and-socket joint 30 has a spherical interior/cavity/socket 31 and a threaded rear opening 32 and a non-threaded front opening 33. The rear opening 32 is threaded to receive the threaded set screw 40 (the set screw 40 having a configured socket 42 in its top surface), while the front opening 33 is not threaded to allow the shaft 46 and tip 47 of the peg 44 to extend therethrough and thus be universally rotationally and angularly positioned relative thereto. The set screw 40 has a spherical inner surface/seat 41.

The first component 12 is characterized by a generally cylindrical piston body 50 having a generally cylindrical interior 57 forming an axial cavity, the body 50 sized for adjustable axial receipt and movement in the interior axial cavity 17 of the body 16 of the second component 14 and having an end 51 with an opening 52 sized and configured to allow receipt of an adjustment bolt 55 of an adjustment collar, clamp, C-clip, C-clamp, or the like 54 for axial length adjustment between the first and second components 12, 14. The bolt 55 allows axial adjustment within the axial slot 18 of the body 16. Because bolt 55 extends through the end 51, axial movement of the clamp 54 causes axial movement of the first component 12 relative to the second component 14. Tightening of the bolt 55 via hex head 56 fixes the axial position of the first component 12 relative the second component 14. The clamp 54 and the bolt/bolt head 55/56 provide an axial sub-strut/component adjustor.

A rod 58 having external threads 59 is axially movably retained in the axial cavity 57 and connected to an axial rod adjustment means 65 via an internally threaded neck 66. Rotation of the neck 66 moves the rod 58 axially up or down depending on the direction of rotation. The neck 66 is part of collar 60 of the adjustment means 65. The collar 60 mostly surrounds the upper portion of the body 50 past the radial flange 53 which provides an axial stop for downward axial travel of the collar 60 on and relative to the body 50. The collar 60 includes a cavity 61 having a spring 62 that is connected via arm (dual or single) 63 that is connected to a push button 64. The arm 63 cooperates between the collar 60 and the threaded shaft 58 to allow and not allow rotation between the two. The spring 62 normally biases the arm/button 63/64 such that rotation of the collar 60 on the threaded shaft 58 is prohibited. Actuating the button 64 actuates the arm 63 to allow collar 60 rotation. The direction of rotation determines the direction of axial movement of the threaded shaft 58. A "+" [shown in the figures] indicates clockwise movement of the collar 60 providing an axially upward movement of the threaded shaft 58 relative to the collar 60, and thus a dual universal/ball-and-socket joint 70 carried on the distal end of the threaded shaft 58, while a "−" [also shown in the figures] indicates counter-clockwise movement of the collar 60 providing an axially downward movement of the threaded shaft 58 relative to the collar 60, and thus the dual universal/ball-and-socket joint 70. Therefore, the present strut 10 provides double or dual axial length adjustment, one for the two components relative one another, and one for the dual universal/ball-and-socket joint relative to its component.

The top or distal end of the threaded shaft 58 supports a dual universal/ball-and-socket joint 70, characterized by a spherical housing/head 71 extending from a neck 72 with an internally threaded cavity 73 sized for threaded reception on the threaded shaft 58, and having a spherical interior, cavity, or socket 74, a configured bore 77, a ball-and-socket joint 78 received for free rotation in the socket 74 and having a spherical interior, cavity, or socket 79, a peg or attachment member 92 having a spherical head 93 for free rotation receipt in the socket 79, a third set screw 84 for fixing rotational orientation of the ball-and-socket joint 78 relative to the head 71, and a fourth set screw 88 for fixing rotational orientation of the spherical head 93 of the peg 92. The attachment peg 92 is thus rotationally positionable relative to the ball-and-socket joint 78, while the ball-and-socket 78 is rotationally positionable relative to the head 71 for two-step or stage rotational orientation positioning of the attachment member 92 or the strut if the attachment member 92 is considered stationary.

The head 71 has a spherical interior/cavity/socket 74 and a threaded rear opening 75 and a non-threaded front opening 76. The rear opening 75 is threaded to receive the threaded set screw 84 (the set screw 84 having a configured socket 86 in its top surface), while the front opening 76 is not threaded to allow the shaft 94 and tip 95 of the peg 92 to extend therethrough and thus be universally rotationally and angularly positioned relative thereto. The set screw 84 has a spherical inner surface/seat 85. The ball-and-socket joint 78 has a spherical interior/cavity/socket 79 and a threaded rear opening 80 and a non-threaded front opening 81. The rear opening 80 is threaded to receive the threaded set screw 88 (the set screw 88 having a configured socket 90 in its top surface), while the front opening 81 is not threaded to allow the shaft 94 and tip 95 of the peg 92 to extend therethrough and thus be universally rotationally and angularly positioned relative thereto. The set screw 88 has a spherical inner surface/seat 89.

Figure 11:
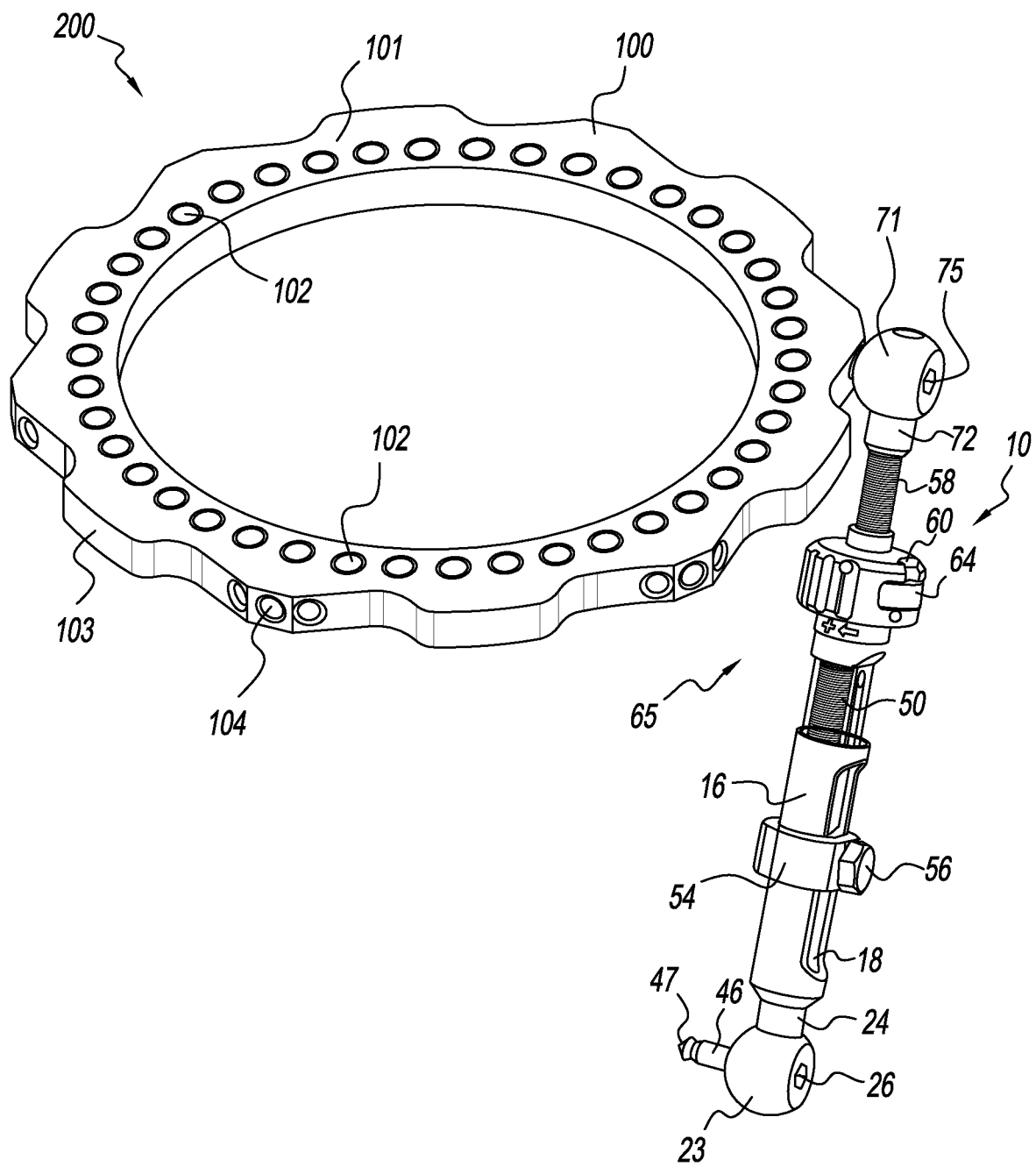
FIG. 11 is an isometric view of the dynamic strut of FIG. 1 connected at its upper dual universal ball joint to a ring fixation component.
Figure 12:
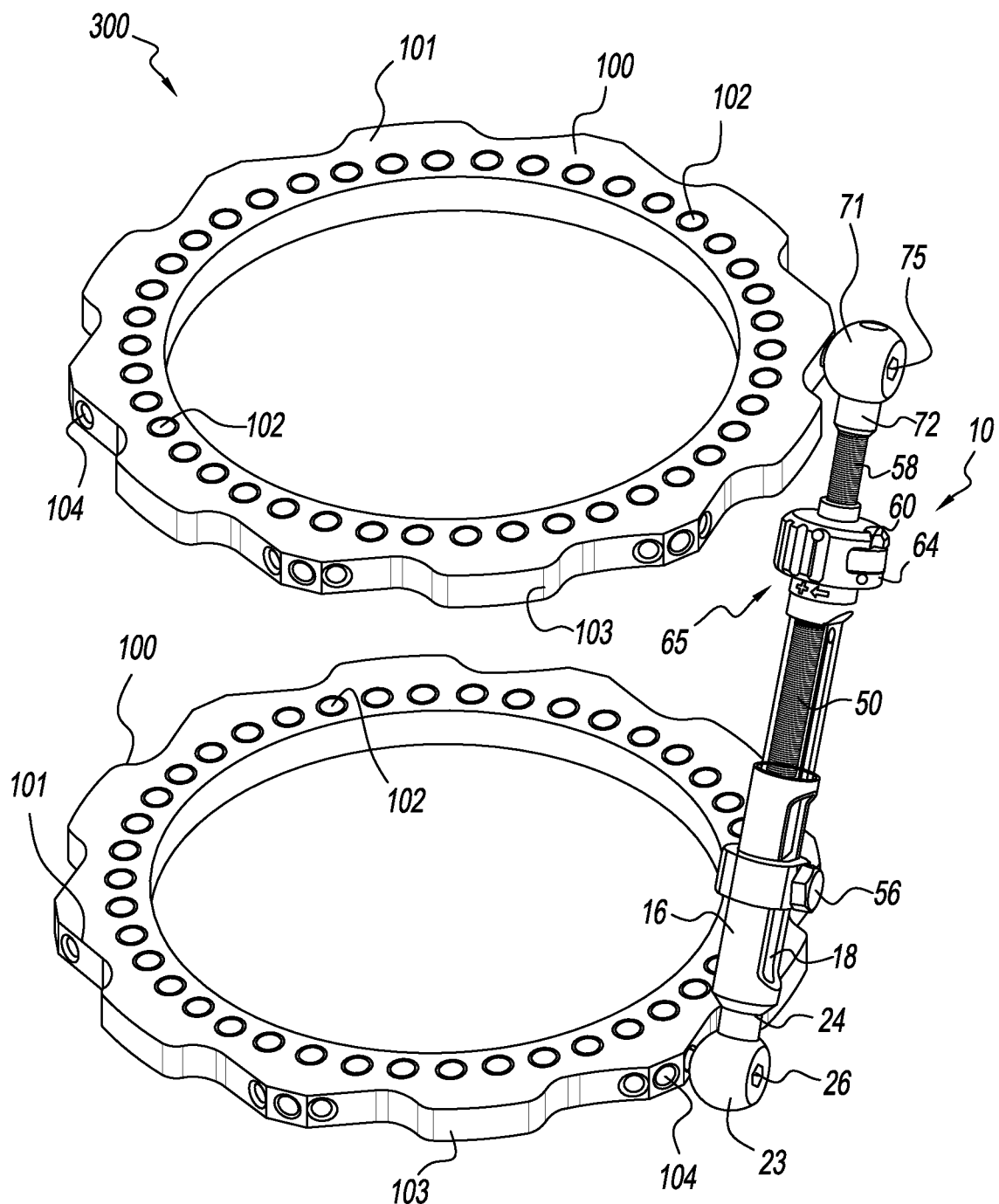
FIG. 12 is an isometric view of the dynamic strut of FIG. 1 connected at its upper dual universal ball joint to a ring fixation component, and at its lower dual universal ball joint to a second ring fixation component.

In FIG. 11, an external fixation/fixator construct 200 is shown with the present dynamic strut 10 connected to an external fixation/fixator ring/component 100, the ring 100 having an upper surface 101 with holes 102, and a side 103 with intermittent connection holes 104. The upper dual universal joint 21 of the strut 10 is shown coupled to the external fixator ring 100 (i.e. the peg of the upper dual universal joint is received in a hole 104). In FIG. 12, an external fixation/fixator construct 300 is shown with the present dynamic strut 10 connected to two (2) external fixation/fixator ring/components 100. More struts may and are typically used in external fixation/fixator constructs.

It should be appreciated that dimensions of the components, structures, and/or features of the present strut may be altered as desired within the scope of the present disclosure.

What is claimed is:

1. A strut for an external fixation construct, the strut comprising:
    a first component characterized by a cylindrical body with a cylindrical interior having a first axial end with an opening into the cylindrical interior at the first axial end of the cylindrical body, a second axial end opposite the first axial end, and an axial slot in a side of the cylindrical body and in communication with the cylindrical interior;
    a first dual universal joint at the second axial end of the cylindrical body, the first dual universal joint having a first head fixed to the second axial end of the cylindrical body and having a first spherical interior, a first ball joint disposed in the first spherical interior and having a second spherical interior, a peg having a spherical head, a shaft extending radially from the spherical head and the first head, and a tip on the shaft distal the spherical head, the tip and shaft configured for reception by an external fixation ring, the spherical head rotationally received in the second spherical interior to allow universal positioning of the tip relative to the first head, a first set screw received in the first ball joint for fixing angular orientation of the peg relative to the first ball joint, and a second set screw received in the first head for fixing angular orientation of the first ball joint relative to the first head;
    a second component characterized by a piston axially movably disposed in the cylindrical interior of the first component, the piston having an end disposed in the cylindrical interior of the first component and having an axial interior, a threaded shaft axially movably disposed in the axial interior of the piston and having a first end disposed in the axial interior of the piston and a second end opposite the first end, and an adjustment means carried on the piston and threadedly coupled to the threaded shaft whereby rotation of the adjustment means axially moves the threaded shaft;
    a second dual universal joint at the second end of the threaded shaft, the second dual universal joint having a second head threadedly attached to the second end of the threaded shaft and having a third spherical interior, a second ball joint disposed in the third spherical interior and having a fourth spherical interior, a second peg having a second spherical head, a second shaft extending radially from the second spherical head and the second head, and a second tip on the second shaft distal the second spherical head, the second tip and second shaft configured for reception by an external fixation ring, the second spherical head rotationally received in the third spherical interior to allow universal positioning of the second tip relative to the second head, a third set screw received in the second ball joint for fixing angular orientation of the second peg relative to the second ball joint, and a fourth set screw received in the second head for fixing angular orientation of the second ball joint relative to the second head; and
    an adjuster, coupled to and between the first and second components for adjusting axial orientation of the second component relative to the first component.

2. The strut of claim 1, wherein the adjuster comprises a C-clip.

3. The strut of claim 1, wherein the adjustment means is spring biased in a locked position.

4. The strut of claim 1, wherein rotation of the adjustment means in a first direction axially moves the threaded shaft in a first axial direction, and rotation of the adjustment means in a second direction opposite the first direction axially moves the threaded shaft in a second axial direction opposite the first axial direction.

5. The strut of claim 4, wherein the first direction of adjustment means rotation is clockwise and the first axial direction is upward, and the second direction of adjustment means rotation is counter-clockwise and the second axial direction is downward.

6. The strut of claim 5, wherein the adjustment means includes a threaded collar configured to receive the threaded shaft.

7. The strut of claim 6, wherein the threaded collar is coupled to an end of the adjustment means.

8. The strut of claim 1, wherein a first housing of the first dual universal joint has a first threaded inlet for receiving the first set screw, the first ball joint has a second threaded inlet for receiving the second set screw, a second housing of the second dual universal joint has a third threaded inlet for receiving the third set screw, and second ball joint has a fourth threaded inlet for receiving the fourth set screw.

9. The strut of claim 8, wherein the first threaded inlet is opposite a first outlet of the first housing, the second threaded inlet is opposite a second outlet of the first ball joint, the third threaded inlet is opposite a third outlet of the second housing, and the fourth threaded inlet is opposite a fourth outlet of the second ball joint.

10. The strut of claim 1, wherein the second component has demarcations along its axial length that, along with the first component, indicate axial length of the strut.

11. The strut of claim 10, wherein the end of the piston in the cylindrical interior of the first component is configured to cooperate with the adjuster.

12. The strut of claim 11, wherein the adjuster comprises:
a band extending around the first component; and
a threaded bolt extending through the first and second components and configured to compress the band to fix axial orientation of the first and second components, and to expand the band to allow adjustment of axial orientation of the first and second components.

13. A strut for an external fixation construct, the strut comprising:
a first sub-strut characterized by a cylindrical body with a cylindrical interior having a first axial end with an opening into the cylindrical interior at the first axial end of the cylindrical body, a second axial end opposite the first axial end, and an axial slot in a side of the cylindrical body and in communication with the cylindrical interior;
a first dual ball-and-socket joint at the second axial end of the cylindrical body, the first dual ball-and-socket joint having a first head fixed to the second axial end of the cylindrical body and having a first spherical socket and a first bore in communication with the first spherical socket, the first bore having a first tapered opening, a first ball joint disposed in the first spherical socket and having a second spherical socket and a second bore in communication with the second spherical socket, the second bore having a second tapered opening, a peg having a spherical head, a shaft extending radially from the spherical head and the first head, and a tip on the shaft distal the spherical head, the tip and shaft configured for reception by an external fixation ring, the spherical head rotationally received in the second spherical socket with the tip and the shaft of the peg extending through the first tapered opening of the first bore of the first spherical socket of the first head and the second tapered opening of the second bore of the second spherical socket of the first ball joint to allow universal positioning of the tip relative to the first head, a first set screw received in the first ball joint for fixing angular orientation of the peg relative to the first ball joint, and a second set screw received in the first head for fixing angular orientation of the first ball joint relative to the first head;
a second sub-strut characterized by a piston axially movably disposed in the cylindrical interior of the first sub-strut, the piston having an end disposed in the cylindrical interior of the first sub-strut and having an axial interior, a threaded shaft axially movably disposed in the axial interior of the piston and having a first end disposed in the axial interior of the piston and a second end opposite the first end, and an adjustment means carried on the piston and threadedly coupled to the threaded shaft whereby rotation of the adjustment means axially moves the threaded shaft;
a second dual ball-and-socket joint at the second end of the threaded shaft, the second dual ball-and-socket joint having a second head threadedly attached to the second end of the threaded shaft and having a third spherical socket and a third bore in communication with the third spherical socket, the third bore having a third tapered opening, a second ball joint disposed in the third spherical socket and having a fourth spherical socket and a fourth bore in communication with the fourth spherical socket, the fourth bore having a fourth tapered opening, a second peg having a second spherical head, a second shaft extending radially from the second spherical head and the second head, and a second tip on the second shaft distal the second spherical head, the second tip and second shaft configured for reception by an external fixation ring, the second spherical head rotationally received in the third spherical socket with the second tip and the second shaft of the second peg extending through the third tapered opening of the third bore of the third spherical socket of the second head and the fourth tapered opening of the fourth bore of the fourth spherical socket of the second ball joint to allow universal positioning of the second tip relative to the second head, a third set screw received in the second ball joint for fixing angular orientation of the second peg relative to the second ball joint, and a fourth set screw received in the second head for fixing angular orientation of the second ball joint relative to the second head; and
an adjuster, coupled to and between the first and second sub-struts for adjusting axial orientation of the second sub-strut relative to the first sub-strut.

14. The strut of claim 13, wherein the adjustment means is spring biased in a locked position.

15. The strut of claim 13, wherein rotation of the adjustment means in a first direction axially moves the threaded shaft in a first axial direction, and rotation of the adjustment means in a second direction opposite the first direction axially moves the threaded shaft in a second axial direction opposite the first axial direction.

16. The strut of claim 15, wherein the first direction of adjustment means rotation is clockwise and the first axial direction is upward, and the second direction of adjustment means rotation is counter-clockwise and the second axial direction is downward.

17. The strut of claim 16, wherein the adjustment means includes a threaded collar configured to receive the threaded shaft.

18. The strut of claim 17, wherein a first housing of the first dual ball-and-socket joint has a first threaded inlet for receiving the first set screw, the first ball joint has a second threaded inlet for receiving the second set screw, a second housing of the second dual ball-and-socket joint has a third threaded inlet for receiving the third set screw, and the second ball joint has a fourth threaded inlet for receiving the fourth set screw.

\* \* \* \* \*